United States Patent [19]

Noponen et al.

[11] Patent Number: 4,601,900

[45] Date of Patent: Jul. 22, 1986

[54] MOUTHWASH COMPOSITION AND A METHOD FOR PREPARING IT

[75] Inventors: Asko K. Noponen; Tapani Pyysalo, both of Espoo, Finland

[73] Assignee: Orion-yhtymä Oy Fermion, Espoo, Finland

[21] Appl. No.: 711,146

[22] Filed: Mar. 13, 1985

[30] Foreign Application Priority Data

Mar. 29, 1984 [FI] Finland .................................. 841252

[51] Int. Cl.$^4$ ............................................... A61K 7/22
[52] U.S. Cl. ........................................................ 424/54
[58] Field of Search ......................................... 424/54

[56] References Cited

U.S. PATENT DOCUMENTS

| | | | |
|---|---|---|---|
| 4,291,017 | 9/1981 | Beierle et al. | 424/52 |
| 4,465,662 | 8/1984 | Sato et al. | 424/54 |
| 4,466,954 | 8/1984 | Ichikawa et al. | 424/50 |
| 4,469,673 | 9/1984 | Iioka et al. | 424/50 |
| 4,486,404 | 12/1984 | Weinert | 424/54 |
| 4,515,772 | 5/1985 | Parran et al. | 424/57 |
| 4,525,343 | 6/1985 | Raaf | 424/54 |

OTHER PUBLICATIONS

Paunio, Makinen, Hurttia, C.A. 101:129041x, 129042y, 129043z, Oct. 8, 1984.
Solheim et al, C.A. 99:187042z (1983).
Addy et al, C.A. 98:149453f (1983).
Van Der Bijl et al, C.A. 98:132142f (1983).
Gjermo et al, C.A. 82:149477m (1975).
Loe, Flotra, C.A. 77:14352t, 14353u (1972).
Flotra et al, C.A. 75:74792e (1971).

*Primary Examiner*—Shep K. Rose
*Attorney, Agent, or Firm*—Burns, Doane, Swecker & Mathis

[57] ABSTRACT

The invention relates to a new mouthwash composition which contains chlorhexidine and xylitol to cover the bitter taste of chlorhexidine. The invention also relates to a method for the preparation of the mouthwash.

6 Claims, No Drawings

MOUTHWASH COMPOSITION AND A METHOD FOR PREPARING IT

The present invention relates to a new mouthwash composition which is anticariogenic and contains chlorhexidine, and a method for preparing it.

Chlorhexidine is a known compound which has been used also in mouthwashes because of its anticariogenic action and its curative action on gingivitis. Chlorhexidine is otherwise suitable for this purpose, but owing to its repulsive bitter taste a mouthwash containing it tastes unpleasant. So far it has not been known how to eliminate the bitter taste or to cover it effectively.

The object of the present invention is to provide a mouthwash composition which is pleasant to use in spite of the chlorhexidine. Therefore, xylitol, which has surprisingly been found to cover the bitter taste of chlorhexidine effectively, is used in the mouthwash according to the invention.

The characteristics of the mouthwash composition, as well as of the method presented for its preparation, are given in the accompanying claims.

The new mouthwash composition according to the invention is water-based in the conventional manner. In this case the most recommendable form of chlorhexidine is gluconate, although acetate is also suitable. In addition to chlorhexidine it is possible to use in the mouthwash conventional auxiliary agents and additives, of which ethyl alcohol can be mentioned as an example.

The amount of xylitol used is determined by how well the presented amount is capable of covering the bitter taste of the chlorhexidine amount used in each case. For conventional chlorhexidine concentrations used (about 0.1–0.2%) a xylitol amount of 2–15% by weight is sufficient. The amount of xylitol is greatly dependent on the effect desired.

At low xylitol contents the bitter taste of chlorhexidine may still be felt too much, whereas high xylitol contents may sweeten the mouthwash too much or be unnecessary in the sense that after a certain concentration hardly any improvement occurs in the taste. The most recommendable content is 5–8% by weight.

By means of the idea according to the invention, i.e. the use of xylitol, two advantages over known compositions are gained. In addition to covering the taste of chlorhexidine, xylitol has been reported to serve in some situations even as an agent which promotes remineralization of tooth enamel. This occurs in spite of the fact that xylitol is a sugar alcohol. Thus, xylitol is an especially suitable additive for use in oral hygiene.

The following examples illustrate the invention without limiting it in any way.

EXAMPLE 1

A mouthwash having the following composition was prepared:

| | |
|---|---|
| Chlorhexidine gluconate | 0.1 g |
| Xylitol | 3.1 g |
| Ethyl alcohol | 5.0 g |
| Distilled water ad | 100 ml |

EXAMPLE 2

A mouthwash was prepared using the following composition:

| | |
|---|---|
| Chlorhexidine gluconate | 0.2 g |
| Xylitol | 6.7 g |
| Ethyl alcohol | 7.0 g |
| Distilled water ad | 100 ml |

EXAMPLE 3

Also a mouthwash having the following composition was prepared:

| | |
|---|---|
| Chlorhexidine acetate | 0.1 g |
| Xylitol | 6.0 g |
| Ethyl alcohol | 5.0 g |
| Distilled water ad | 100 ml |

The mouthwash was prepared by mixing the said substances with each other and by adding up to 100 ml of water, as well as by ensuring proper dissolving.

We claim:

1. An aqueous anticariogenic mouthwash composition consisting of water, ethyl alcohol, conventional auxiliary agents and additives and from about 0.1 to 0.2% by weight of the entire composition of a salt of chlorhexidine selected from the group consisting of chlorhexidine gluconate and chlorhexidine acetate and mixtures thereof and from about 2 to 15% by weight of xylitol to cover the bitter taste of said salt of chlorhexidine.

2. The composition according to claim 1 wherein the amount of xylitol ranges from about 5 to 8% by weight.

3. The composition according to claim 1 wherein said salt of chlorhexidine is chlorhexidine gluconate.

4. In a method for the elimination of the bitter taste of a salt of chlorhexidine in an aqueous chlorhexidine anticariogenic mouthwash composition the improvement which consists essentially of the step of dissolving about 2 to 15% by weight of the entire composition of bitter taste masking xylitol as the essential taste-making component in water containing conventional auxiliary agents and additive and about 0.1 to 0.2% by weight of an otherwise unpleasant and repulsive bitter-tasting salt of chlorhexidine selected from the group consisting of chlorhexidine gluconate and chlorhexidine acetate and mixtures thereof.

5. The method according to claim 4 wherein the amount of xylitol ranges from about 5 to 8% by weight.

6. The method according to claim 4 wherein said salt of chlorhexidine is chlorhexidine gluconate.

* * * * *